United States Patent
Kikuchi et al.

(10) Patent No.: US 10,768,089 B2
(45) Date of Patent: Sep. 8, 2020

(54) PARTICLE COLLECTING APPARATUS AND PARTICLE COLLECTING SYSTEM

(71) Applicant: TOKYO ELECTRON LIMITED, Tokyo (JP)

(72) Inventors: Toshihiko Kikuchi, Miyagi (JP); Nobuyuki Nagayama, Miyagi (JP); Hikaru Kikuchi, Miyagi (JP); Katsushi Abe, Miyagi (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 398 days.

(21) Appl. No.: 15/719,178

(22) Filed: Sep. 28, 2017

(65) Prior Publication Data

US 2018/0095021 A1    Apr. 5, 2018

(30) Foreign Application Priority Data

Oct. 3, 2016 (JP) ................. 2016-195730

(51) Int. Cl.

| | |
|---|---|
| *G01N 15/10* | (2006.01) |
| *G01N 33/00* | (2006.01) |
| *H01L 21/67* | (2006.01) |
| *G01N 15/06* | (2006.01) |

(Continued)

(52) U.S. Cl.
CPC ............ *G01N 15/10* (2013.01); *G01N 15/06* (2013.01); *G01N 33/0014* (2013.01); *H01L 21/67028* (2013.01); *H01L 21/6838* (2013.01); *G01N 2015/0046* (2013.01)

(58) Field of Classification Search
CPC .......... G01N 1/24; G01N 15/06; G01N 15/10; G01N 2015/0046; G01N 33/0014; H01L 21/02057; H01L 21/67028; H01L 21/6838; B08B 5/20; B08B 5/04
USPC ............... 134/21; 15/339; 269/21; 294/64.3; 414/752.1; 73/864.33
See application file for complete search history.

(56) References Cited

U.S. PATENT DOCUMENTS 2,238,541 A * 4/1941 Spagnolo ............ A61H 9/0021
                                                   15/397
3,915,739 A * 10/1975 Maahs ...................... B08B 5/02
                                                   134/21

(Continued)

FOREIGN PATENT DOCUMENTS

| JP | 10-185795 A | 7/1998 |
|---|---|---|
| JP | 2003-17422 A | 1/2003 |

(Continued)

*Primary Examiner* — Joseph J Hail
*Assistant Examiner* — Arman Milanian
(74) *Attorney, Agent, or Firm* — Rothwell, Figg, Ernst & Manbeck, P.C.

(57) ABSTRACT

A particle collecting apparatus includes a cylindrical housing, a gap forming unit, a supply port and an intake port. The cylindrical housing has a closed top and an open bottom facing a target object. The gap forming unit is configured to form a gap having a predetermined distance between the bottom and the target object. The supply port is formed at the opening of the bottom in an annular shape along an inner wall of the housing and configured to supply a gas to the target object. The intake port is provided closer to a central axis of the supply port than the supply port and configured to suck particles on the target object.

11 Claims, 19 Drawing Sheets

(51) Int. Cl.
*H01L 21/683* (2006.01)
*G01N 15/00* (2006.01)

(56) References Cited

U.S. PATENT DOCUMENTS

| | | | | |
|---|---|---|---|---|
| 4,735,449 | A * | 4/1988 | Kuma | B65G 47/911 |
| | | | | 294/64.3 |
| 5,457,847 | A * | 10/1995 | Uzawa | B08B 5/026 |
| | | | | 15/345 |
| 6,643,893 | B2 * | 11/2003 | Momonoi | B08B 5/02 |
| | | | | 15/102 |
| 8,695,156 | B2 * | 4/2014 | Marshall | F15D 1/00 |
| | | | | 15/339 |
| 9,061,304 | B2 * | 6/2015 | Miller | B23K 26/1476 |
| 2004/0197433 | A1 * | 10/2004 | Terada | B08B 7/0042 |
| | | | | 425/174.4 |
| 2005/0205699 | A1 * | 9/2005 | Bezama | B08B 3/02 |
| | | | | 239/754 |
| 2007/0032088 | A1 * | 2/2007 | Yamamoto | G01N 1/24 |
| | | | | 438/709 |
| 2007/0199580 | A1 * | 8/2007 | Hasebe | B08B 5/04 |
| | | | | 134/21 |
| 2013/0074281 | A1 * | 3/2013 | Takahashi | A47L 9/00 |
| | | | | 15/339 |
| 2016/0035563 | A1 * | 2/2016 | Lin | H01L 21/02057 |
| | | | | 156/345.54 |
| 2017/0136576 | A1 * | 5/2017 | Ashihara | B08B 5/04 |

FOREIGN PATENT DOCUMENTS

| | | |
|---|---|---|
| JP | 2006-278367 A | 10/2006 |
| JP | 2013-71083 A | 4/2013 |

\* cited by examiner

FIG.11

| NO. | h₁(mm) | h₂(mm) | w(mm) | COLLECTING RATE |
|---|---|---|---|---|
| 0 | – | – | – | 56.5 |
| 1 | 40 | 50 | 1.5 | 90.9 |
| 2 | 30 | 40 | 1.5 | 93.3 |
| 3 | 30 | 40 | 3.0 | 82.9 |
| 4 | 20 | 30 | 1.5 | 89.0 |
| 5 | 20 | 30 | 3.0 | 87.5 |
| 6 | 20 | 23.3 | 3.0 | 90.4 |

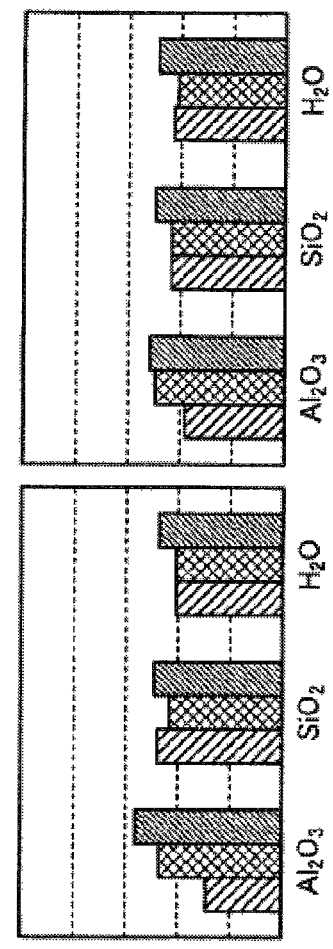
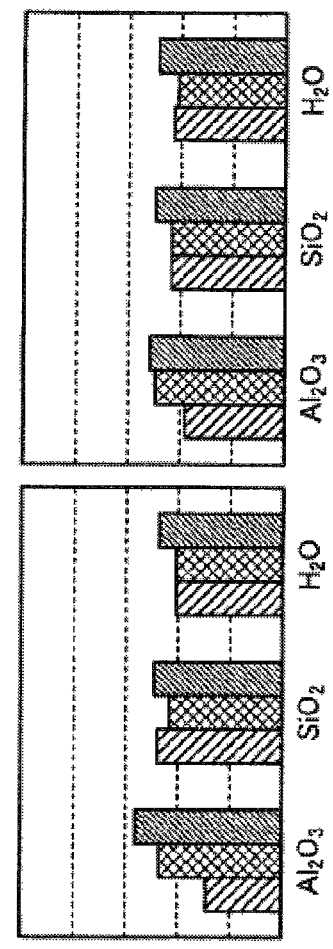
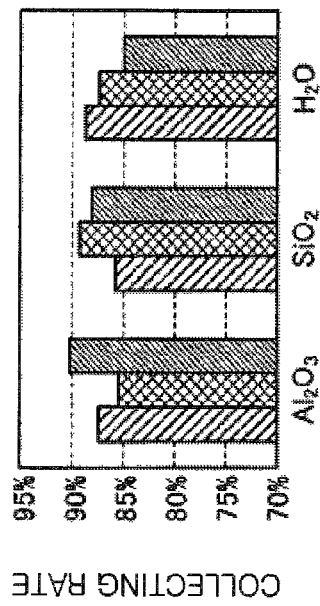
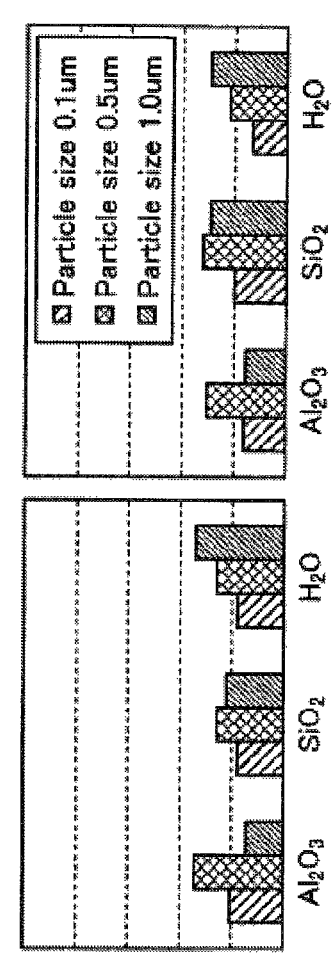
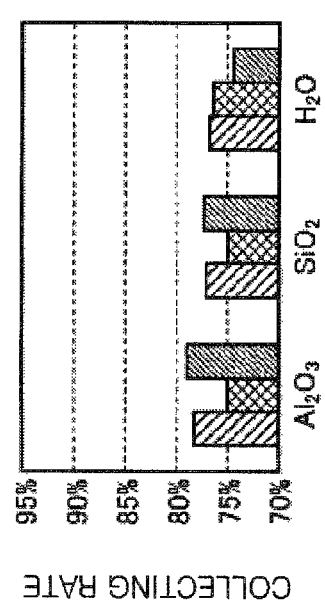
FIG. 12A FIG. 12B FIG. 12C FIG. 12D FIG. 12E FIG. 12F

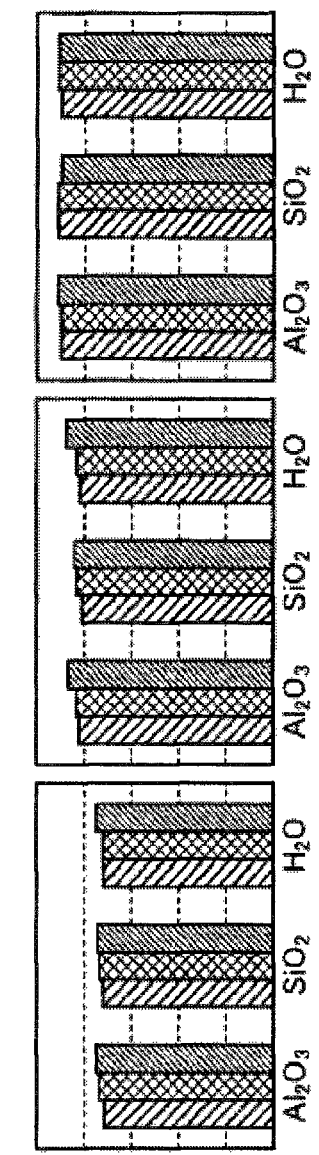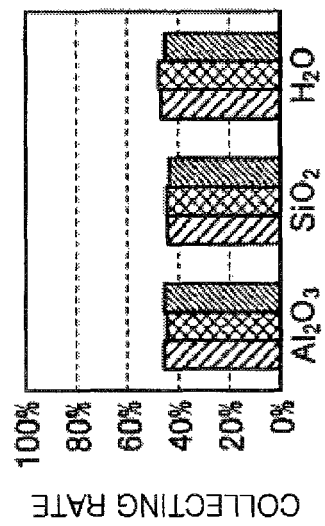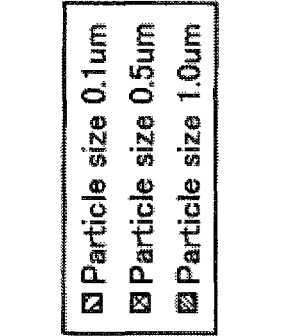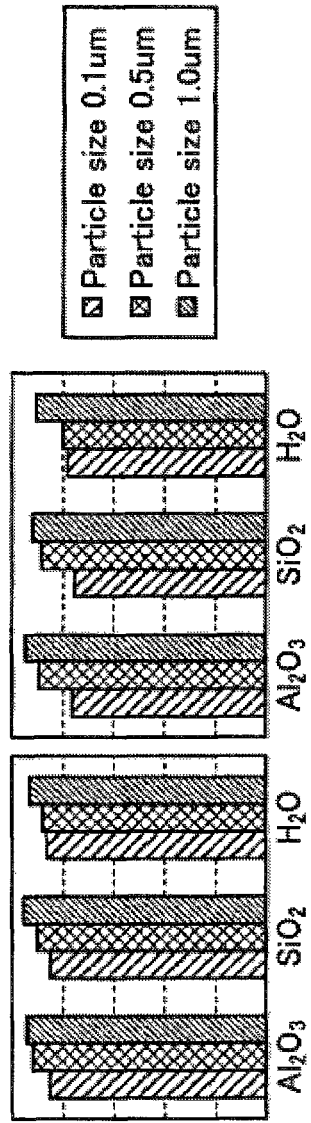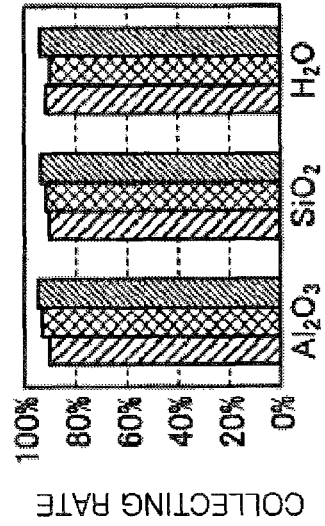
FIG. 14A  FIG. 14B  FIG. 14C  FIG. 14D  FIG. 14E  FIG. 14F  FIG. 14G

PARTICLE COLLECTING APPARATUS AND PARTICLE COLLECTING SYSTEM

CROSS-REFERENCE TO RELATED APPLICATIONS

This application claims priority to Japanese Patent Application No. 2016-195730 filed on Oct. 3, 2016, the entire contents of which are incorporated herein by reference.

FIELD OF THE INVENTION

The disclosure relates to a particle collecting apparatus, a particle collecting method, and a particle collecting system.

BACKGROUND OF THE INVENTION

As for a tool for evaluating a manufactured semiconductor device or components in a semiconductor manufacturing apparatus after use, there is known a particle collecting apparatus for collecting particles deposited on a surface of a semiconductor device or the like (see, e.g., Japanese Patent Application Publication No. 2013-71083). This particle collecting apparatus is brought into contact with the semiconductor device or the like as an evaluation target, forms a sealed space on the surface of the semiconductor device or the like, and supplies a gas into the sealed space. Further, the particle collecting apparatus collects particles deposited on the surface of the semiconductor device or the like by peeling off the particles deposited on the surface of the semiconductor device or the like by using the supplied gas and sucking gas containing the peeled-off particles. The particle collecting apparatus includes an ultrasonic wave generator and can effectively peel off the particles deposited on the surface of the semiconductor device or the like by using an ultrasonic wave emitted from the ultrasonic wave generator.

Since, however, it is required to bring a conventional particle collecting apparatus into contact with the target object in order to form a sealed space, the semiconductor or the like as the evaluation target may be contaminated or damaged. The conventional particle collecting apparatus may be used without contact with the semiconductor device or the like as the evaluation target. In that case, however, the sealed space is not formed on the surface of the semiconductor device or the like. As a consequence, a collecting rate of the particles is decreased. In addition, the particles deposited on the surface of the semiconductor device or the like are scattered by the gas supplied from the particle collecting apparatus. As a result, another contamination may occur at the semiconductor device or the like.

SUMMARY OF THE INVENTION

In accordance with an aspect, there is provided a particle collecting apparatus including a cylindrical housing, a gap forming unit, a supply port and an intake port. The cylindrical housing has a closed top and an open bottom facing a target object. The gap forming unit is configured to form a gap having a predetermined distance between the bottom and the target object. The supply port is formed at the opening of the bottom in an annular shape along an inner wall of the housing and configured to supply a gas to the target object. The intake port is provided closer to a central axis of the supply port than the supply port and configured to suck particles on the target object.

In accordance with various aspects and embodiments of the present disclosure, it is possible to effectively collect the particles on the target object without contact with the target object.

BRIEF DESCRIPTION OF THE DRAWINGS

The objects and features of the disclosure will become apparent from the following description of embodiments, given in conjunction with the accompanying drawings, in which:

FIG. 11 shows exemplary results of simulation of collection efficiency in the case of varying a height of the supply line, a height of the intake line and a width of the supply port;

FIGS. 12A to 12F show exemplary results of simulation of collection efficiency in the case of varying a flow rate of a supplied gas with respect to a flow rate of a sucked gas;

FIGS. 14A to 14G show exemplary results of simulation of collection efficiency in the case of varying a flow rate;

DETAILED DESCRIPTION OF THE EMBODIMENTS

Figure 1:
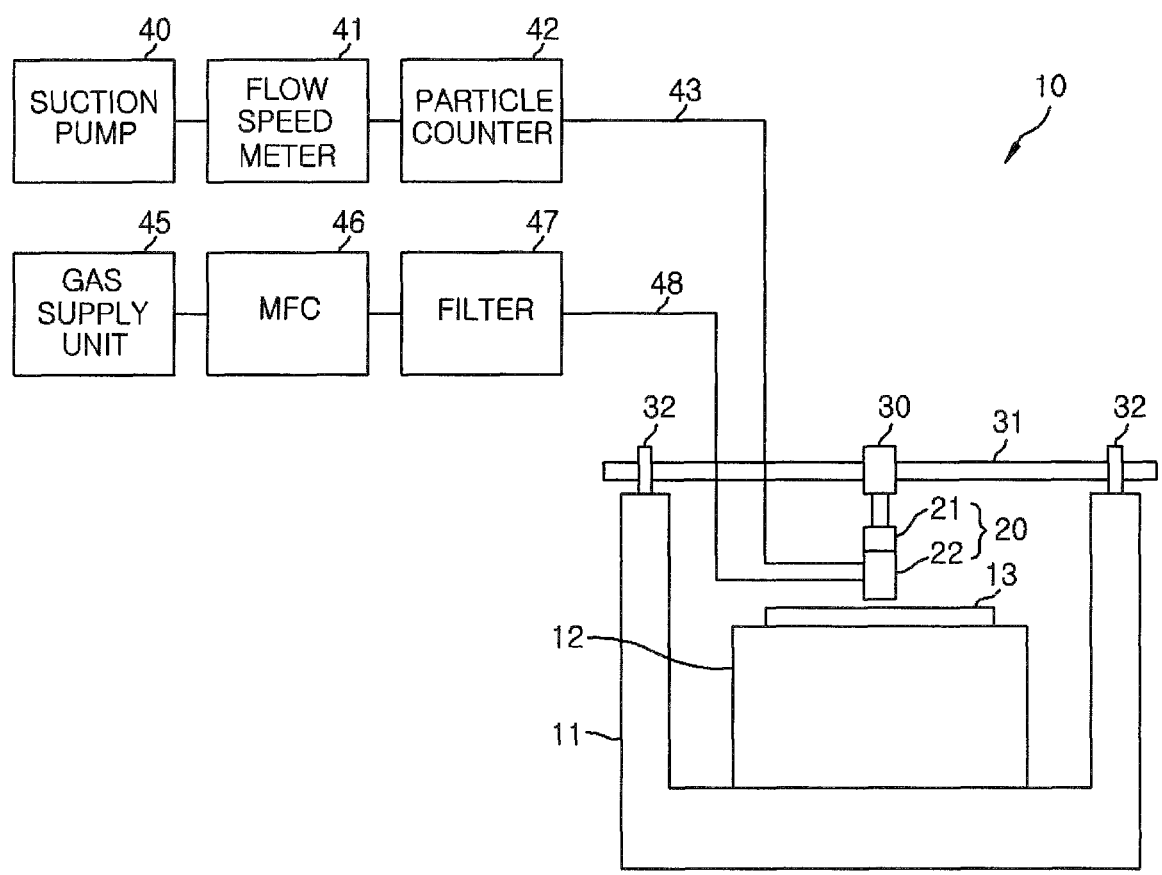
FIG. 1 is a system configuration diagram showing an example of a particle collecting system.

A particle collecting apparatus in accordace with one embodiment includes a cylindrical housing, a gap forming unit, a supply port and an intake port. The cylindrical housing has a closed top and an open bottom facing a target object. The gap forming unit is configured to form a gap having a predetermined distance between the bottom and the target object. The supply port is formed at the opening of the bottom in an annular shape along an inner wall of the housing and configured to supply a gas to the target object. The intake port is provided closer to a central axis of the supply port than the supply port and configured to suck particles on the target object.

The particle collecting apparatus may further include a cylindrical member disposed along a central axis of the supply port.

The cylindrical member may be an ultrasonic wave generator configured to generate an ultrasonic wave toward the target object.

In the particle collecting apparatus, a shock wave pressure applied to a surface of the target object by the ultrasonic wave generated by the ultrasonic wave generator may be 150 dB or above.

The particle collecting apparatus may further include a partition plate configured to partition a gas supplied to the supply port and a gas sucked from the intake port; a first flow path, through which a gas supplied from an outside of the housing flows toward the supply port, formed between an inner wall surface of the housing and an outer wall surface of the partition plate, the first flow path having a ceiling that is gradually decreased while rotating about the central axis of the supply port in a direction in which the gas supplied from the outside of the housing flows; and a second flow path, through which the gas sucked from the intake port flows toward the outside of the housing, formed between an inner wall surface of the partition plate and an outer wall surface of the cylindrical member, the second flow path having a ceiling that is gradually increased while rotating about the cylindrical member in a direction in which the gas sucked from the intake port flows.

The gas flowing through the first flow path may flow from top to bottom while rotating in a predetermined direction along the inner wall surface of the housing about the central axis of the supply port, and the gas flowing through the second flow path may flow from bottom to top while rotating in a direction same as the direction of the gas flows through the first flow path along the inner wall surface of the partition plate about the central axis of the intake port.

In the particle collecting apparatus, a wind speed of a gas on the target object may be 0.02 mm/sec or above.

In the particle collecting apparatus, a ratio of a flow rate of the gas supplied through the supply port to a flow rate of the gas sucked through the intake port may be greater than or equal to 1.0 and smaller than or equal to 1.2.

In the particle collecting apparatus, the housing may have a substantially cylindrical shape, the supply port may be inclined toward the central axis of the supply port at the bottom of the housing, and an angle of the inclination of the supply port with respect to the bottom of the housing may be within a range specified by $\tan^{-1}(d_1/2r)<\theta\leq 60°$, wherein r is a radius of the bottom of the housing and $d_1$ is a distance between the bottom of the housing and the target object.

In the particle collecting apparatus, the gas supplied from the supply port may be dry air or inert gas.

A particle collecting method in accordance with one embodiment includes forming a gap having a predetermined distance between a target object and a cylindrical housing having a closed top and an open bottom facing the target object; supplying a gas to the target objet from a supply port formed at the opening of the bottom in an annular shape along an inner wall surface of the housing; and sucking particles on the target object from an intake port positioned closer to a central axis of the supply port than the supply port.

A particle collecting system in accordance with one embodiment includes a particle collecting apparatus; a gas supply unit configured to supply a gas to the particle collecting apparatus; a flow rate controller configured to control a flow rate of the gas supplied from the gas supply unit to the particle collecting apparatus; a suction pump configured to suck the gas from the particle collecting apparatus; and a flow speed meter configured to measure a flow speed of the gas sucked from the particle collecting apparatus by the suction pump. The particle collecting apparatus includes: a cylindrical housing having a closed top and an open bottom facing a target object; a gap forming unit configured to form a gap having a predetermined distance between the bottom and the target object; a supply port formed at the opening of the bottom in an annular shape along an inner wall surface of the housing and configured to supply the gas supplied from the gas supply unit to the target object; and an intake port provided closer to a central axis of the supply port than the supply port and configured to suck a gas containing particles on the target object by suction of the suction pump.

The particle collecting system may further include: a particle counter provided between the particle collecting apparatus and the flow speed meter and configured to measure the number of particles contained in a gas sucked through the particle collecting apparatus.

Hereinafter, embodiments of a particle collecting apparatus, a particle collecting method and a particle collecting system will be described in detail with reference to the accompanying drawings. However, the particle collecting apparatus, the particle collecting method and the particle collecting system are not restricted by the following embodiments.

(Configuration of Particle Collecting System 10)

FIG. 1 is a system configuration diagram showing an example of a particle collecting system 10. As shown in FIG. 1, for example, the particle collecting system 10 includes: a particle collecting apparatus 20, a suction pump 40, a flow speed meter 41, a particle counter 42, a gas supply unit 45, a mass flow controller (MFC) 46, a filter 47. FIG. 1 illustrates a state in which the particle collecting apparatus 20 or the like is installed at an upper portion of the chamber 11 which is opened after a predetermined process is performed on a semiconductor wafer 13 mounted on a mounting table 12 in a chamber 11.

The particle collecting apparatus 20 includes an adjustment unit 21 and a head 22. The head 22 is connected to lines 43 and 48. The gas supply unit 45 supplies a gas to a surface of the semiconductor wafer W as an example of an evaluation target. The gas supplied from the gas supply unit 45 is, e.g., dry air or inert gas. The inert gas may be, e.g., argon gas, nitrogen gas or the like. A flow rate of the gas supplied from the gas supply unit 45 is controlled by the MFC 46. The gas having a flow rate controlled by the MFC 46 is purified by a filter 47 and then supplied to the head 22 through the line 48.

The suction pump 40 is connected to the head 22 via the flow speed meter 41, the particle counter 42 and the line 43. The suction pump 40 sucks a gas between the head 22 and the semiconductor wafer 13 from a bottom surface of the head 22. The flow speed meter 41 measures a flow speed of the gas sucked by the suction pump 40. The particle counter 42 measures the number of particles contained in the gas sucked from the bottom surface of the head 22.

The head 22 is disposed such that the bottom surface thereof faces the semiconductor wafer 13. A gas supplied through the line 48 is injected from a supply port formed at the bottom surface of the head 22 onto the semiconductor wafer 13. The head 22 sucks the gas containing particles on the semiconductor wafer 13 from an intake port formed at the bottom surface of the head 22 by a suction operation of the suction pump 40 and allows the sucked gas to flow toward the particle counter 42 through the line 43.

The adjustment unit 21 adjusts a distance between a moving unit 30 and the head 22, thereby forming a gap of a predetermined distance between the bottom surface of the head 22 and the semiconductor wafer 13. The adjustmnet unit 21 is an example of a gap forming unit.

Figure 2:
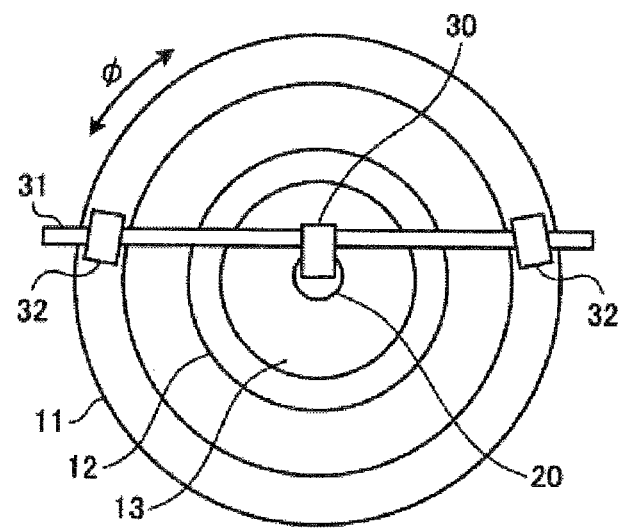
FIG. 2 is a top view showing an example of an installation state of a particle collecting apparatus.

The moving unit 30 holds the particle collecting apparatus 20 against a guide 31. The moving unit 30 can change a position thereof on the guide 31 while moving along the guide 31. A moving unit 32 holds the guide 31. As shown in FIG. 2, for example, the moving unit 32 can change a direction ϕ of the guide 31 while moving along a sidewall of the chamber 11. FIG. 2 is a top view showing an exemplary installation state of the particle collecting apparatus 20. The particle collecting apparatus 20 can be moved to a certain position on the semiconductor wafer 13 by controlling the moving units 30 and 32 with a control unit (not shown). A particle generating location on the semiconductor wafer 13 can be specified by matching the position of the particle collecting apparatus 20 on the semiconductor wafer 13 and the number of particles collected by the particle collecting apparatus 20.

In the present embodiment, the particle collecting apparatus 20 collects particles on the semiconductor wafer as an example of the target object to be evaluated. However, the target object is not limited to the semiconductor wafer 13. The particle collecting apparatus 20 may collect particles deposited on the components of the semiconductor manufacturing apparatus, such as the electrostatic chuck, the sidewall of the chamber 11 and the like.

An operation of the particle collecting system 10 configured as described above is generally controlled by a control unit (not shown). The control unit includes a processor, a user interface and a storage unit. The processor has a CPU (Central Processing Unit) or the like and controls the respective components of the particle collecting system 10. The user interface includes a keyboard for an operator to input commands to operate the particle collecting system 10, a display for visualizing an operational status of the particle collecting system 10, and the like. The storage unit stores therein a control program, data and the like for executing various processes performed by the particle collecting system 10 under the control of the controller.

The processor performs following processes by reading out and executing the control program or the like stored in the storage unit. In other words, the processor moves the particle collecting apparatus 20 to a predetermined location on the semiconductor wafer 13 by controlling the moving units 30 and 32. The processor ensures a gap having a predetermined distance between the bottom surface of the head 22 and the semiconductor wafer 13 by controlling the adjustment unit 21. The processor allows the flow speed meter 41 to read out a flow speed of the gas sucked by the suction pump 40 by operating the suction pump 40 and the flow speed meter 41. The processor controls a suction amount of the suction pump 40 such that the flow speed read out by the flow speed meter 41 becomes a flow speed corresponding to a predetermined flow rate. The processor controls the MFC 46 such that the flow rate of the gas injected from the bottom surface of the head 22 becomes a predetermined flow rate by operating the gas supply unit 45. Further, the processor operates the particle counter 42 to obtain data indicating the number of particles measured by the particle counter 42.

(Configuration of Particle Collecting Apparatus 20)

Figure 3:
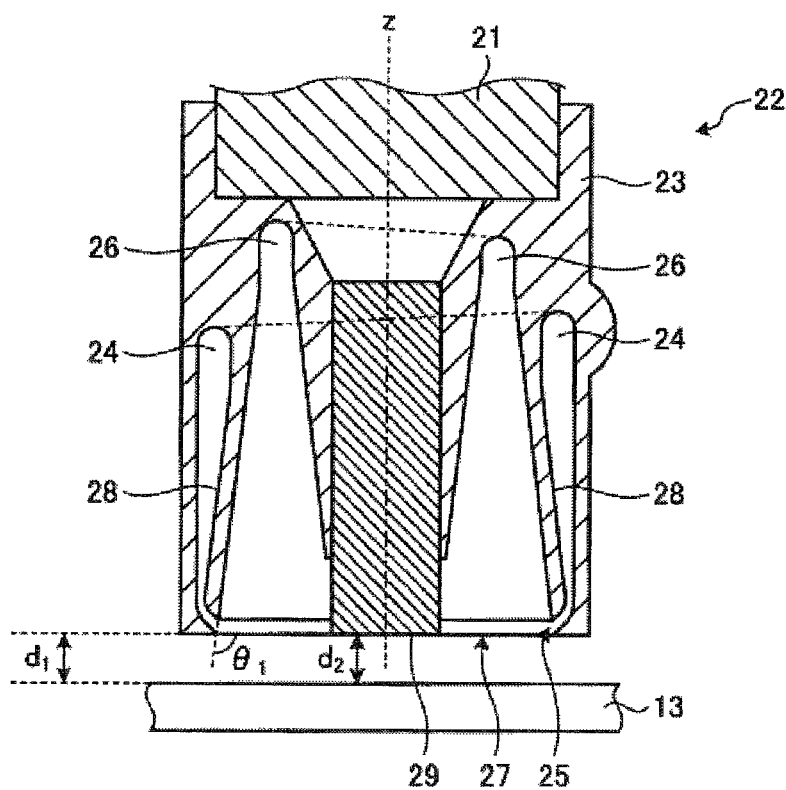
FIG. 3 shows an exemplary cross section of a head of the particle collecting apparatus.
Figure 4:
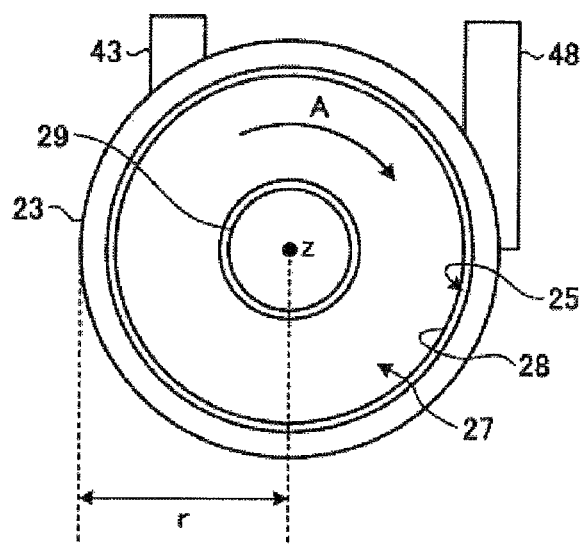
FIG. 4 shows an exemplary bottom surface of the head of the particle collecting apparatus.

FIG. 3 shows an exemplary cross section of the head 22 of the particle collecting apparatus 2. FIG. 4 shows an exemplary bottom surface of the head 22 of the particle collecting apparatus 20. The head 22 has a substantially cylindrical housing 23 having a lower opening facing the semiconductor wafer 13 and a closed top. A central axis of the housing 23 is defined as a Z-axis. As shown in FIG. 4, for example, a radius on a bottom surface of the housing 23 is defined as r.

The housing 23 is made of, e.g., a lightweight material having a low dielectric constant. The housing 23 may be made of, e.g., conductive polytetrafluoroethylene, conductive polyimide, conductive ABS (Acrylonitrile Butadiene Styrene) resin, aluminum alloy, conductive polycarbonate resin or the like. In the case of using these materials, it is possible to suppress particles from being adsorbed on the housing 23 due to electrostatic charge. It is preferable to perform mirroring treatment on the surface of the housing 23 by, e.g., electrolytic polishing or the like. By performing the mirroring treatment on the surface of the housing 23, the adhesion of particles onto the surface of the housing 23 is suppressed.

As shown in FIGS. 3 and 4, for example, a supply port for supplying a gas to the semiconductor wafer 13 is formed at the lower opening of the housing 23 in an annular shape along an inner wall surface of the housing 23. In the present embodiment, a central axis of the supply port 25 coincides with the Z-axis. The supply port 25 communicates with a supply line 24 for supplying a gas supplied from the outside of the housing 23 through the line 48 to the supply port 25.

As shown in FIGS. 3 and 4, for example, an intake port for sucking a gas containing particles on the semiconductor wafer 13 is formed at the lower opening of the housing 23. The intake port 27 is closer to the Z-axis that is the central axis of the supply port 25, compared to the supply port 25. The intake port 27 communicates with an intake line 26 for allowing the gas sucked through the intake port 27 to flow toward the outside of the housing 23.

A substantially cylindrical partition plate 28 for partitioning the gas flowing through the supply line 24 and the gas flowing through the intake line 26 is provided inside the housing 23. In the present embodiment, an angle $\theta_1$ between an inner surface of the partition plate 28 and the bottom surface of the housing 23 is greater than 90°, as can be seen from FIG. 3, for example.

As shown in FIG. 3, for example, the supply line 24 is formed between the inner wall surface of the housing 23 and an outer wall surface of the partition plate 28. A ceiling of the supply line 24 is gradually decreased while rotating about the central axis (Z-axis in the present embodiment) of the supply port 25 in a direction in which the gas supplied from the outside of the housing 23 through the line 48 flows. Accordingly, the gas supplied from the outside of the housing 23 into the supply line 24 through the line 48 flows in a spiral shape from top to bottom while rotating about the central axis of the supply port 25 and is injected from the supply port 25 to the semiconductor wafer 13. The supply line 24 is an example of a first flow path.

As shown in FIG. 3, for example, the intake line 26 is formed between the inner wall surface of the partition plate 28 and an outer wall surface of an ultrasonic wave generator

29. A ceiling of the intake line 26 is gradually increased while rotating about the ultrasonic wave generator 29 in a direction in which the gas sucked from the intake port 27 flows. Accordingly, the gas sucked from the bottom of the housing 23 through the intake port 27 flows in a spiral shape from bottom to top while rotating about the ultrasonic wave generator 29 in the intake line 26 in a direction indicated by an arrow A shown in FIG. 4, for example, and is sucked by the suction pump 40 through the line 43. The intake line 26 is an example of a second flow path.

The ultrasonic wave generator 29 is provided in the housing 23 along the Z-axis that is the central axis of the supply port 25. In the present embodiment, the ultrasonic wave generator 29 has a substantially cylindrical shape. The ultrasonic wave generator 29 generates an ultrasonic wave and emits the generated ultrasonic wave to the semiconductor wafer 13. Accordingly, particles adhered onto the surface of the semiconductor wafer 13 are peeled off. A frequency of the ultrasonic wave generated by the ultrasonic wave generator 29 is, e.g., 15 kHz to 1 MHz, and preferably, e.g., 15 kHz to 200 kHz. The ultrasonic wave generator 29 is an example of a cylindrical member. In the present embodiment, as shown in FIG. 3, for example, a distance $d_1$ between the lower end of the housing 23 and the semiconductor wafer 13 is equal to a distance $d_2$ between the lower end of the ultrasonic wave generator 29 and the semiconductor wafer 13. When the distance $d_1$ is smaller than the distance $d_2$, the distance $d_1$ and the distance $d_2$ may be different from each other.

Figure 5:
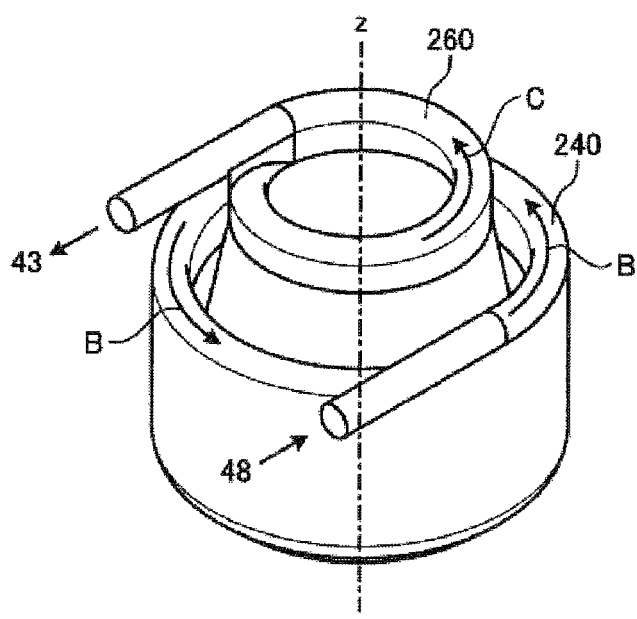
FIGS. 5 to 8 explain exemplary shapes of a space in a supply line and a space in an intake line.
Figure 6:
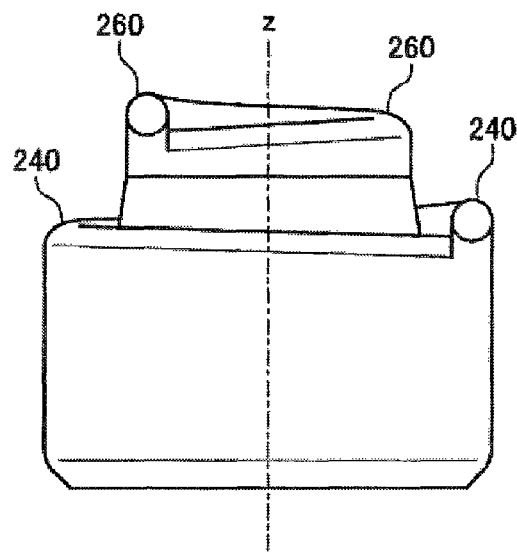
Figure 7:
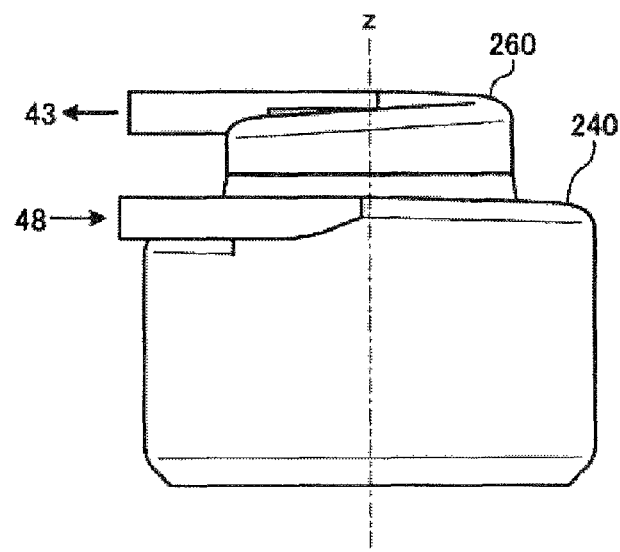
Figure 8:
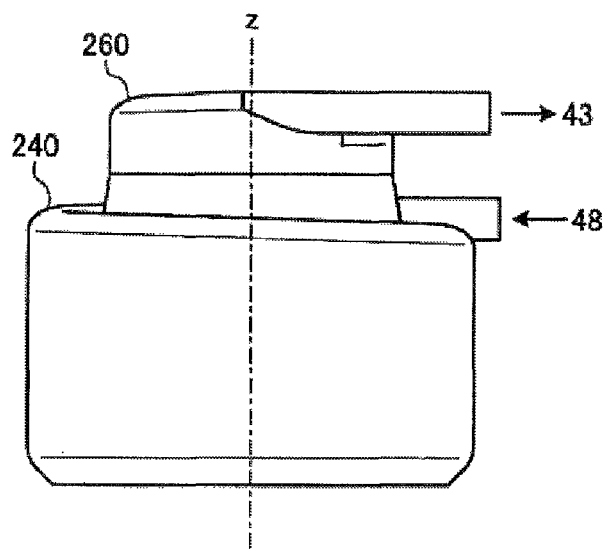

FIGS. 5 to 8 explain an example of a space 240 in the supply line 24 and an example of a space 260 in the intake line 26. FIG. 5 is a perspective view showing the example of the spaces 240 and 260. FIG. 6 is a front view showing the examples of the spaces 240 and 260. FIG. 7 is a right side view showing the example of the spaces 240 and 260. FIG. 8 is a left side view showing the examples of the spaces 240 and 260.

As shown in FIGS. 5 to 8, for example, a height of the space 240 in the supply line 24 is gradually decreased while rotating about the Z-axis in a direction in which the gas supplied through the line 48 flows (direction indicated by arrow B in FIG. 5). As shown in FIG. 5, for example, in the space 240, the gas is supplied from the line 48 in a tangential direction of the substantially annular space 240 when viewed from the Z-axis direction. Accordingly, the gas supplied from the outside of the housing 23 into the supply line 24 through the line 48 flows in a spiral shape from top to bottom while rotating about the Z-axis in the direction indicated by the arrow B, for example.

As shown in FIGS. 5 to 8, for example, a height of the space 260 in the intake line 26 is gradually increased while rotating about the Z-axis in a direction in which the gas sucked through the line 43 flows (direction indicated by arrow C in FIG. 5). As shown in FIG. 5, for example, in the space 260, the gas is sucked through the line 43 in a tangential direction of the substantially annular space 260 when viewed from the Z-axis direction. Accordingly, the gas sucked from the bottom of the housing 23 flows in a spiral shape from bottom to top while rotating about the Z-axis in the intake line 26 in the direction indicated by the arrow C in FIG. 5, for example. The rotating direction of the gas flowing in the space 240 and the rotating direction of the gas flowing in the space 260 are identical to each other when viewed from the Z-axis direction, as shown in FIG. 5, for example.

Figure 9:
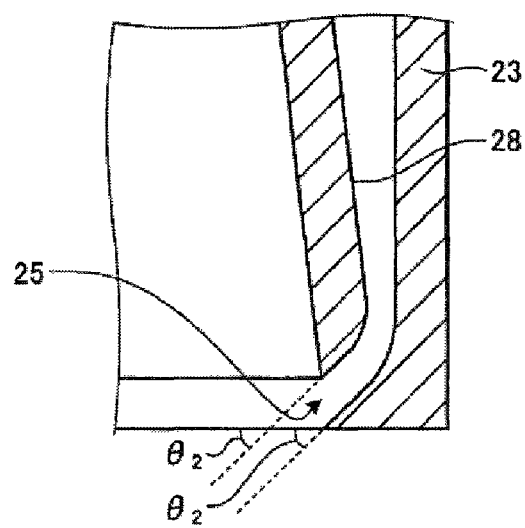
FIG. 9 is an enlarged cross sectional view for explaining exemplary inclination of a supply port.

In the present embodiment, as shown in FIG. 9, for example, the supply port 25 is inclined toward the central axis of the supply port 25 (Z-axis in the present embodiment). FIG. 9 is an enlarged cross sectional view for explaining exemplary inclination of the supply port 25. An angle of the inclination of the supply port 25 with respect to the bottom surface of the housing 23 is defined as $\Theta_2$.

The gas supplied into the supply line 24 flows in the space 240 in the supply line 24 in a spiral shape from top to bottom. Then, the gas is injected from the annular supply port 25 in an inclined direction toward the central axis of the supply port 25 and supplied onto the semiconductor wafer 13. The gas supplied onto the semiconductor wafer 13 peels off particles on the semiconductor wafer 13 and is sucked through the intake port 27 positioned closer to the central axis of the supply port than the supply port 25. Then, the gas flows in the space 260 in the intake line 26 in a spiral shape from bottom to top and is sucked by the suction pump 40 through the line 43.

Below the housing 23, the gas is supplied from the supply port 25 in a downwardly inclined direction toward the Z-axis direction and the supplied gas is sucked near the Z-axis. Accordingly, diffusion of the particles peeled-off by the gas supplied from the supply port 25 to an outer region of a region below the head 22 on the semiconductor wafer 13 is suppressed. In other words, the gas supplied from the supply port 25 functions as an air curtain. Therefore, the diffusion of particles which is caused by the gas supply can be suppressed.

The gas that has flown in the space 240 in the supply line 24 in a spiral shape from top to bottom and has been injected from the supply port 25 onto the semiconductor wafer 13 is sucked through the intake port 27 and flows in the space 260 in the intake line 26 in a spiral shape from bottom to top. Therefore, vortex of gas in a predetermined direction (in the present embodiment, a counterclockwise direction when viewed from above along the Z-axis) is generated below the housing 23. Accordingly, the gas supplied from the supply port 25 onto the semiconductor wafer 13 is effectively sucked through the intake port 27 without stagnating at the lower portion of the housing 23. As a consequence, the particles peeled-off by the gas supplied from the supply port 25 are effectively collected through the intake port 27.

(Simulation Result)

Figure 10:
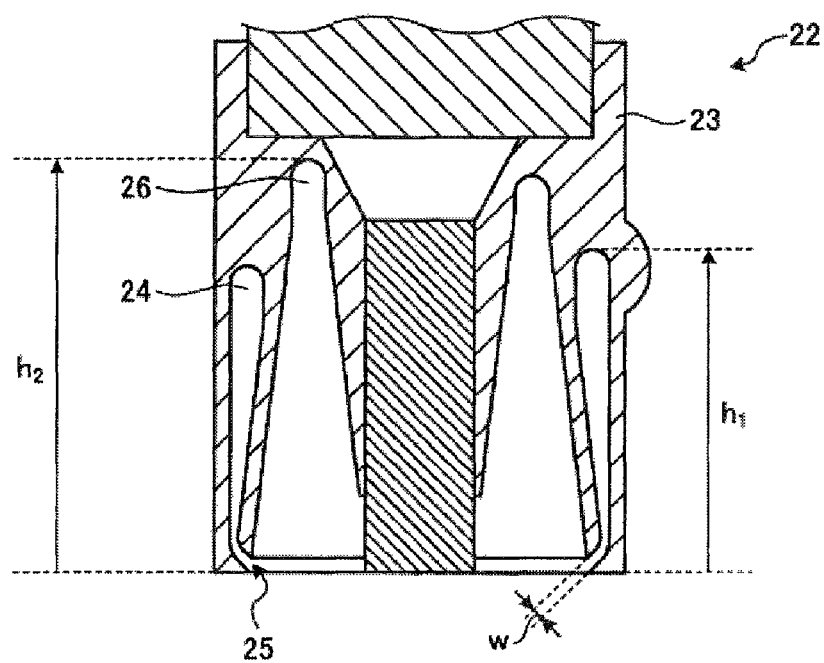
FIG. 10 explains an exemplary height of the supply line, an exemplary height of the intake line and an exemplary width of the supply port.

Next, the collecting rate of particles in the case of varying a height $h_1$ of the supply line 24, a height $h_2$ of the intake line 26, and a width w of the supply port 25 in the head 22 was simulated. FIG. 10 explains examples of the height $h_1$ of the supply line 24, the height $h_2$ of the intake line 26, and the width w of the supply port 25.

FIG. 11 shows an example of a result of the simulation of the collecting rate in the case of varying the height $h_1$ of the supply line 24, the height $h_2$ of the intake line 26, and the width w of the supply port 25. In FIG. 11, a collecting rate measured by a conventional particle collecting apparatus for collecting particles while being in contact with a target object, which was provided to be spaced apart from the semiconductor wafer 13 by a distance $d_1$, is shown, as a comparative example, in column No. "0". The collecting rate indicates a ratio of collected particles among the particles existing on the target object. As for the conventional particle collecting apparatus, a particle collecting apparatus disclosed in, e.g., Japanese Patent Application Publication No. 2013-71083, was used.

The other conditions in the simulation shown in FIG. 11 are set as follows.

Distance $d_1$ between the bottom surface of the housing 23 and the semiconductor wafer 13: 2 mm Angle $\theta_2$ of the inclination of the supply port 25 with respect to the bottom surface of the housing 23: 45°

Type of gas supplied from the supply port 25: dry air flow rate of the gas supplied from the supply port 25: 28.3 L/min Flow rate of the gas sucked from the intake port 27: 28.3 L/min Material forming the particles: $Al_2O_3$ Particle size: 0.1 μm In the following, the simulation was performed under the above condition, unless particularly mentioned.

Referring to the simulation result of FIG. 11, the collecting rate of particles in the particle collecting apparatus 20 of the present embodiment was higher than that in the conventional particle collecting apparatus by 30% or more regardless of the values of the height $h_1$ of the supply line 24, the height $h_2$ of the intake line 26 and the width w of the supply port 25 which are shown in FIG. 11. The collecting rate of particles can be increased to 90% or more by controlling the height $h_1$ of the supply line 24, the height $h_2$ of the intake line 26 and the width w of the supply port 25. In an actual case of manufacturing the conventional particle collecting apparatus corresponding to No. "0" in FIG. 11 and the particle collecting apparatus 20 corresponding to No. "5" in FIG. 11 and measuring the collecting rate of particles, the same measurement result as that shown in FIG. 11 was obtained. Therefore, the particle collecting apparatus 20 of the present embodiment can effectively collect particles on the target object without contact with the target object.

Next, the collecting rate of particles was simulated while varying a ratio $Q_1/Q_2$ of a flow rate $Q_1$ of a gas supplied from the supply port 25 and a flow rate $Q_2$ of a gas sucked from the intake port 27. FIGS. 12A to 12F show exemplary results of simulations of the collecting rate in the case of varying the flow rate $Q_1$ of the supplied gas with respect to the flow rate $Q_2$ of the sucked gas.

In the simulations shown in FIGS. 12A to 12F, the flow rate $Q_2$ of the gas sucked from the intake port 27, i.e., the flow rate $Q_2$ of the gas sucked by the suction pump 40, was fixed to 28.3 L/min, and the flow rate $Q_1$ of the gas supplied from the supply port 25, i.e., the flow rate $Q_1$ of the gas supplied from the gas supply unit 45 was varied. Further, in the simulations shown in FIGS. 12A to 12F, aluminum oxide ($Al_2O_3$), silicon dioxide ($SiO_2$), and water ($H_2O$) were used as materials forming the particles to be collected. In addition, in the simulations shown in FIGS. 12A to 12F, the particle size (diameter) was set to 0.1 μm, 0.5 μm and 1.0 μm, and the collecting rate in each particle size was simulated.

FIG. 12A shows the collecting rate in the case of setting the flow rate $Q_1$ of the gas supplied from the supply port 25 to 28.3 L/min which is the same as the flow rate $Q_2$ of the gas sucked from the intake port 27. FIG. 12B shows the collecting rate in the case of setting the flow rate $Q_1$ of the gas supplied from the supply port 25 to 31.1 L/min which is greater than the flow rate $Q_2$ of the gas sucked from the intake port 27 by 10%. FIG. 12C shows the collecting rate in the case of setting the flow rate $Q_1$ of the gas supplied from the supply port 25 to 34.0 L/min which is greater than the flow rate $Q_2$ of the gas sucked from the intake port 27 by 20%. FIG. 12D shows the collecting rate in the case of setting the flow rate $Q_1$ of the gas supplied from the supply port 25 to 36.8 L/min which is greater than the flow rate $Q_2$ of the gas sucked from the intake port 27 by 30%. FIG. 12E shows the collecting rate in the case of setting the flow rate $Q_1$ of the gas supplied from the supply port 25 to 39.6 L/min which is greater than the flow rate $Q_2$ of the gas sucked from the intake port 27 by 40%. FIG. 12F shows the collecting rate in the case of setting the flow rate $Q_1$ of the gas supplied from the supply port 25 to 42.5 L/min which is greater than the flow rate $Q_2$ of the gas sucked from the intake port 27 by 50%.

Figure 13:
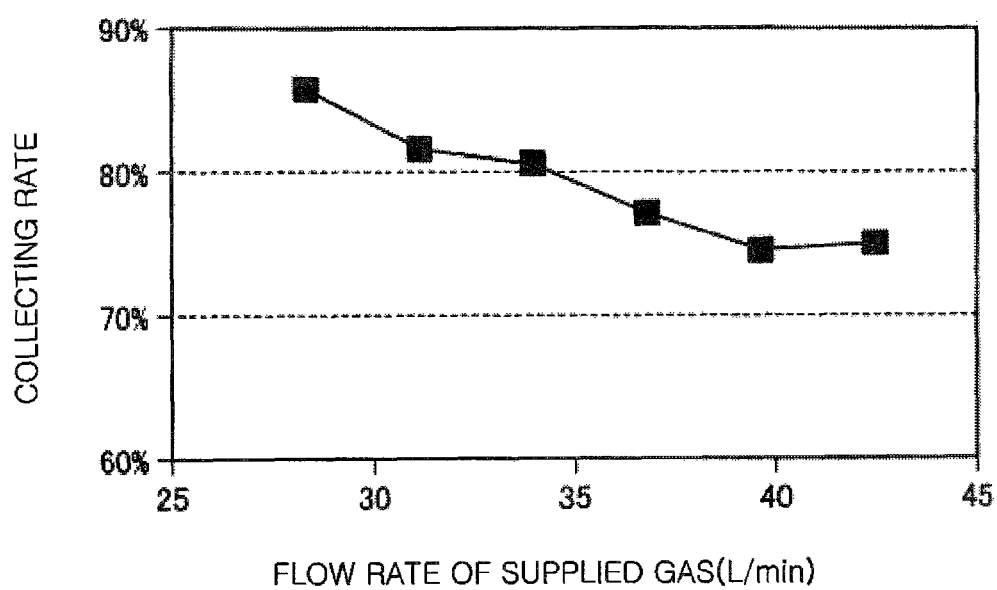
FIG. 13 summarizes a result of $SiO_2$ among the simulation results shown in FIGS. 12A to 12F.

Referring to FIGS. 12A to 12F, it is clear that when the flow rate $Q_1$ of the gas supplied from the supply port 25 is equal to the flow rate $Q_2$ of the gas sucked from the intake port 27, the collecting rate of particles is highest. It is also clear that the collecting rate tends to be decreased as the flow rate $Q_1$ of the gas supplied from the supply port 25 becomes greater than the flow rate $Q_2$ of the gas sucked from the intake port 27 regardless of sizes or types of the particles. The result of $SiO_2$ among the simulation results shown in FIGS. 12A to 12F is summarized in FIG. 13, for example. Referring to FIG. 13, the collecting rate of particles can be maintained at 80% or more when the flow rate $Q_1$ of the gas supplied from the supply port 25 is greater than the flow rate $Q_2$ of the gas sucked from the intake port 27 by 20%, i.e., when the flow rate $Q_1$ is 34.0 L/min or less. Therefore, it is preferable that the ratio $Q_1/Q_2$ of the flow rate $Q_1$ of the gas supplied from the supply port 25 to the flow rate $Q_2$ of the gas sucked from the intake port 27 satisfies a condition $$1.0 \leq (Q_1/Q_2) \leq 1.2.$$

When the flow rate $Q_2$ of the gas sucked from the intake port 27 is set to be greater than the flow rate $Q_1$ of the gas supplied from the supply port 25, a gas around the particle collecting apparatus 20 is sucked by the intake port 27. Therefore, particles other than the particles on the target object below the particle collecting apparatus 20 are also collected, which makes it difficult to accurately measure the number of particles existing on the target object below the particle collecting apparatus 20. Accordingly, it is preferable to set the flow rate $Q_2$ of the gas sucked from the intake port 27 to be smaller than the flow rate $Q_1$ of the gas supplied from the supply port 25.

From the results shown in FIGS. 12A to 12F and 13, it is clear that the collecting rate becomes highest when the flow rate $Q_1$ of the gas supplied from the supply port 25 is equal to the flow rate $Q_2$ of the gas sucked from the intake port 27. Thus, the collecting rate in the case of setting the flow rate $Q_1$ of the gas supplied from the supply port 25 to be equal to the flow rate $Q_2$ of the gas sucked from the intake port 27 and varying the flow rates $Q_1$ and $Q_2$ was simulated. FIGS. 14A to 14G show exemplary results of the simulations of the collecting rate in the case of varying the flow rates.

In the simulations shown in FIGS. 14A to 14G, as in the simulation shown in FIGS. 12A to 12F, $Al_2O_3$, $SiO_2$ and $H_2O$ were used as materials forming the particles to be collected and the particle size was set to 0.1 μm, 0.5 μm and 1.0 μm. The collecting rate in each particle size was simulated.

FIG. 14A shows the collecting rate in the case of setting the flow rates $Q_1$ and $Q_2$ to 14.2 L/min. FIG. 14B shows the collecting rate in the case of setting the flow rates $Q_1$ and $Q_2$ to 21.2 L/min. FIG. 14C shows the collecting rate in the case of setting the flow rates $Q_1$ and $Q_2$ to 28.3 L/min. FIG. 14D shows the collecting rate in the case of setting the flow rates $Q_1$ and $Q_2$ to 35.4 L/min. FIG. 14E shows the collecting rate in the case of setting the flow rates $Q_1$ and $Q_2$ to 42.5 L/min. FIG. 14F shows the collecting rate in the case of setting the flow rates $Q_1$ and $Q_2$ to 49.5 L/min. FIG. 14G shows the collecting rate in the case of setting the flow rates $Q_1$ and $Q_2$ to 56.6 L/min.

Figure 15:
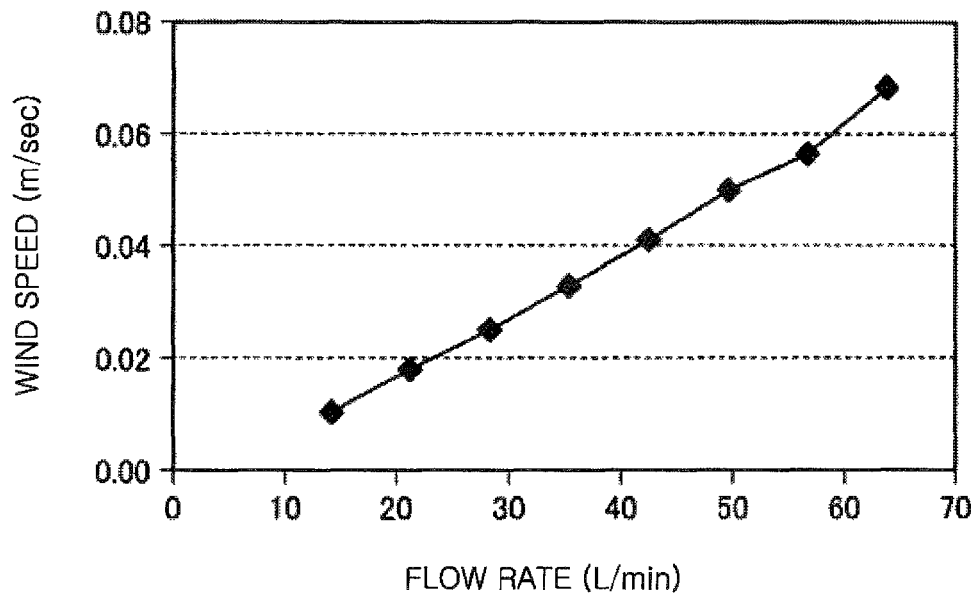
FIG. 15 shows exemplary relation between a flow rate and a wind speed on a target object.

The wind speed on the target object in the case of supplying and sucking the gases at the flow rates shown in FIGS. 14A to 14G is illustrated as a graph shown in FIG. 15, for example. FIG. 15 shows exemplary relation between the flow rate and the wind speed on the target object. The target object indicates a region on the semiconductor wafer 13 which is formed when a bottom surface of the ultrasonic wave generator 29 is projected from above on the semiconductor wafer 13 in the Z-axis direction. Referring to FIG. 15, the wind speed of the gas on the target object is increased as the flow rates of the supplied gas and the sucked gas are increased.

Figure 16:
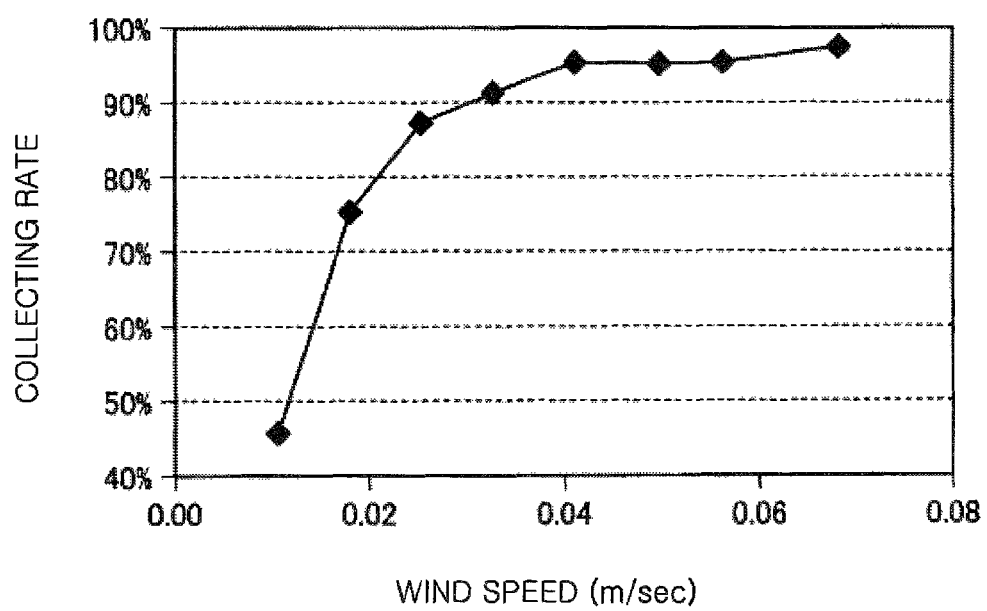
FIG. 16 shows exemplary relation between a wind speed on the target object and collection efficiency.

Next, the collecting rate of particles with respect to the wind speed of the gas shown in FIG. 15 is illustrated as a graph in FIG. 16, for example. FIG. 16 shows exemplary relation between the wind speed on the target object and the collecting rate. In FIG. 16, the collecting rate of $Al_2O_3$ is used as the collecting rate of particles. Referring to FIG. 16, the collecting rate is increased as the wind speed is increased within a range in which the wind speed is low, whereas the collecting rate is converted to a constant value within a range in which the wind speed is high. Further, referring to FIG. 16, when the wind speed of the gas on the target object is 0.02 m/sec or above, the collecting rate becomes 80% or above. Therefore, it is preferable to control the flow rate of the gas supplied from the supply port 25 and the flow rate of the gas sucked from the intake port 27 such that the wind speed of the gas on the target object becomes 0.02 m/sec or above.

Figure 17:
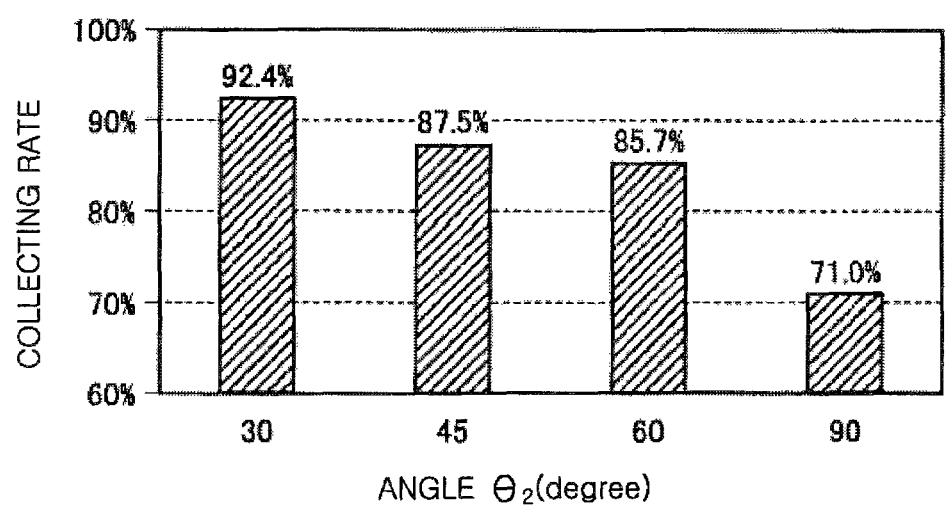
FIG. 17 shows an exemplary result of simulation of collection efficiency in the case of varying an angle of the supply port.

Next, the collecting rate in the case of varying the angle $\theta_2$ of the inclination of the supply port 25 was simulated. As shown in FIG. 9, for example, the supply port 25 is inclined at the angle $\theta_2$ with respect to the bottom surface of the housing 23. FIG. 17 shows an exemplary result of the simulation of the collecting rate in the case of varying the angle $\theta_2$ of the supply port 25.

Referring to FIG. 17, the collecting rate is decreased as the angle $\theta_2$ of the supply port 25 is increased. In order to maintain the collecting rate at 80% or above, it is preferable that the angle $\theta_2$ of the supply port 25 is 60° or less. Further, referring to FIG. 17, the collecting rate tends to be increased as the angle $\theta_2$ of the supply port 25 is decreased. Here, if the injection direction of the gas from the supply port 25 is directed into a region (hereinafter, referred to as "target region") on the semiconductor wafer 13 which is formed when the bottom surface of the particle collecting apparatus 20 is projected from above on the semiconductor wafer 13 in the Z-axis direction, the gas injected from the supply port 25 is sucked by the intake port 27 formed at the bottom of the particle collecting apparatus 20.

However, if the gas is injected from the supply port 25 toward an outside of the target region, the gas injected from the supply port 25 is diffused to the outside of the target region and a part of the gas injected from the supply port 25 is not sucked by the intake port 27. Therefore, it is preferable that the gas is injected from the supply port 25 toward the target region. In order to inject the gas from the supply port 25 toward the target region, the angle of the supply port 25 needs to be within a range specified by the following relation (1).

$$\tan^{-1}(d_1/2r) < \theta_2 \leq 90° \tag{1}$$

In the above relation (1), $d_1$ indicates a distance between the lower end of the housing 23 and the semiconductor wafer 13 as shown in FIG. 3, and r indicates a radius on the bottom surface of the housing 23 as shown in FIG. 4.

Therefore, it is preferable to set the angle $\theta_2$ of the supply port 25 to be within a range specified by the following relation (2) based on the simulation result shown in FIG. 17 and the above relation (1).

$$\tan^{-1}(d_1/2r) < \theta_2 \leq 60° \tag{2}$$

Figure 18A:
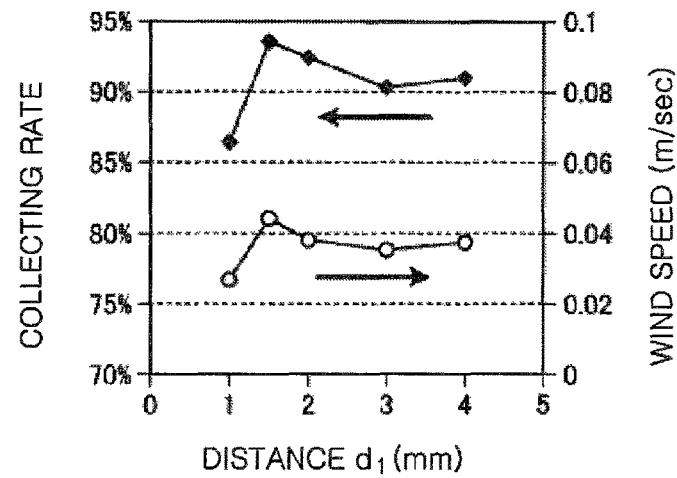
FIGS. 18A to 18C show exemplary results of simulation of a wind speed on the target object and collection efficiency in the case of varying a distance between the particle collecting apparatus and the target object.
Figure 18B:
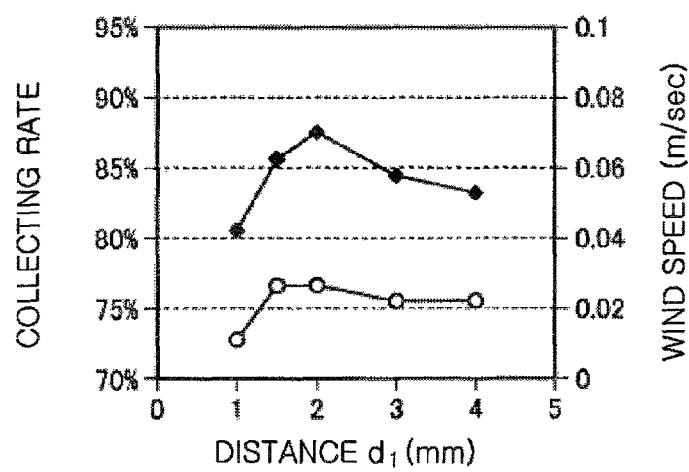
Figure 18C:
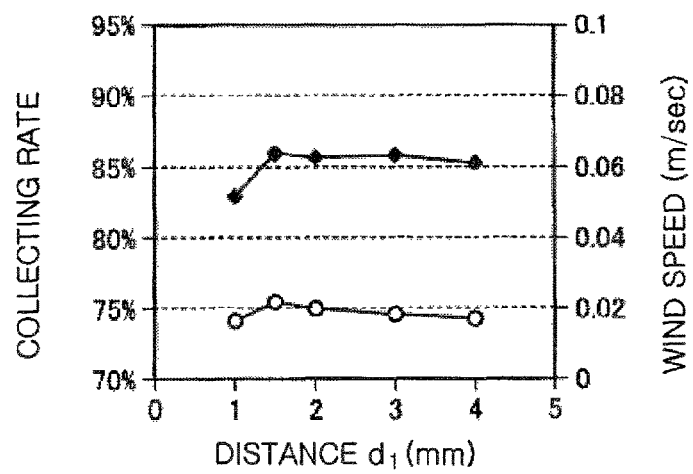

Next, the collecting rate in the case of varying the distance $d_1$ between the bottom surface of the particle collecting apparatus 20 and the semiconductor wafer 13 as the target object was simulated. FIGS. 18A to 18C show exemplary results of the simulation of the collecting rate and the wind speed on the target object in the case of varying the distance $d_1$ between the particle collecting apparatus 20 and the target object. FIG. 18A shows a simulation result obtained when the angle $\theta_2$ of the supply port 25 was 30°; FIG. 18B shows a simulation result obtained when the angle $\theta_2$ of the supply port 25 was 45°; and FIG. 18C shows a simulation result obtained when the angle $\theta_2$ of the supply port 25 was 60°. In FIGS. 18A to 18C, a black quadrangle indicates the collecting rate and a white circle indicates the wind speed. The simulations shown in FIGS. 18A to 18C are performed by using the particle collecting apparatus 20 in which the distance $d_1$ between the bottom surface of the particle collecting apparatus 20 and the semiconductor wafer 13 is equal to the distance $d_2$ between the bottom surface of the ultrasonic wave generator 29 and the semiconductor wafer 13.

Referring to the simulation results shown in FIGS. 18A to 18C, when the distance $d_1$ between the particle collecting apparatus 20 and the semiconductor wafer 13 is within a range from 1 mm to 2 mm, the collecting rate and the wind speed are increased as the distance $d_1$ is increased regardless of the angle $\theta_2$ of the supply port 25. When the distance $d_1$ between the particle collecting apparatus 20 and the semiconductor wafer 13 is within a range from 2 mm to 4 mm, the collecting rate and the wind speed are slightly decreased as the distance $d_1$ is increased.

Referring to the simulation results of FIGS. 18A to 18C, the collecting rate of particles is highest at the distance $d_1$ at which the wind speed is maximum, regardless of the angle $\theta_2$ of the supply port 25. When the distance $d_1$ between the particle collecting apparatus 20 and the semiconductor wafer 13 is decreased, a constant amount of gas flows in a narrow space and, thus, the wind speed is increased. However, if the distance $d_1$ between the particle collecting apparatus 20 and the semiconductor wafer 13 is excessively decreased, a conductance between the particle collecting apparatus 20 and the semiconductor wafer 13 is increased. Thus, the amount of gas flowing into a position immediately below the ultrasonic wave generator 29 is decreased and the amount of gas flowing directly into the intake port 27 is increased. Accordingly, the wind speed of the gas immediately below the ultrasonic wave generator 29 is decreased. The wind speed becomes maximum when the balance between the space into which the gas flows and the conductance is ensured.

Figure 19:
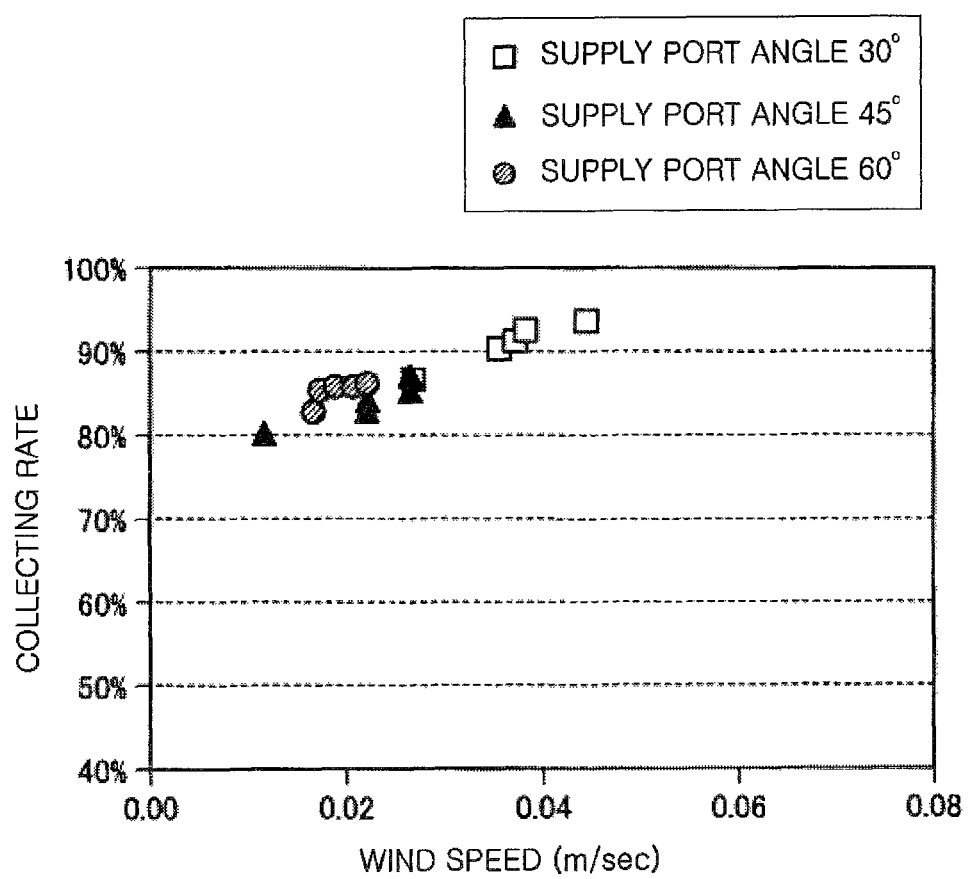
FIG. 19 shows exemplary relation among an angle of the supply port, a wind speed on the target object and collection efficiency.

The graphs shown in FIGS. 18A to 18C are summarized into one graph shown in FIG. 19, for example. FIG. 19 shows exemplary relation among the angle $\theta_2$ of the supply port 25, the wind speed on the target object, and the collecting rate. Referring to FIG. 19, the collecting rate of particles becomes 80% or above when the wind speed on the target object is 0.02 m/sec or above and the angle $\theta_2$ of the supply port 25 is 60° or less.

As clearly understood from the above description on the embodiment of the particle collecting system 10, the particle collecting system 10 of the present embodiment can effectively collect particles on the target object without contact with the target object.

In the particle collecting system 10 of the present embodiment, the substantially cylindrical ultrasonic wave generator 29 is provided at the center of the intake line 26. Therefore, the wind speed between the bottom surface of the ultrasonic wave generator 29 and the semiconductor wafer 13 can be increased. Accordingly, the particles on the semiconductor wafer 13 can be effectively collected.

Further, in the particle collecting system 10 of the present embodiment, an ultrasonic wave having a predetermined frequency and a predetermined amplitude is emitted onto the surface of the semiconductor wafer 13 by the substantially cylindrical ultrasonic wave generator 29 provided at the center of the intake line 26. Accordingly, the particles on the surface of the semiconductor wafer 13 can be separated from the surface of the semiconductor wafer 13 below the ultrasonic wave generator 29. As a result, the particles on the semiconductor wafer 13 can be effectively collected.

Further, in the particle collecting system 10 of the present embodiment, the gas supplied from the gas supply unit 45 flows from top to bottom in the supply line 24 while rotating in a spiral shape about the central axis of the supply port 25 and then is supplied from the supply port 25 onto the semiconductor wafer 13. The gas supplied onto the semiconductor wafer 13 peels off the particles on the semiconductor wafer 13 and then flows from bottom to top in the intake line 26 while rotating in a spiral shape about the central axis of the supply port 25 through the intake port 27 positioned closer to the central axis of the supply port 25 than the supply port 25. Accordingly, vortex flow of the gas is generated between the particle collecting apparatus 20 and the semiconductor wafer 13, and the particles peeled-off by the gas supplied from the supply port 25 are effectively sucked through the intake port 27 and the intake line 26 without being scattered from the region between the particle collecting apparatus 20 and the semiconductor wafer 13 to the outside. As a result, the particles on the semiconductor wafer 13 can be effectively collected.

Further, in the particle collecting system 10 of the present embodiment, the rotating direction of the gas flowing in a spiral shape in the supply line 24 is the same as that of the gas flowing in a spiral shape in the intake line 26 when viewed from the direction of the central axis of the supply port 25. Therefore, the vortex flow of the gas can be effectively generated between the particle collecting apparatus 20 and the semiconductor wafer 13. Accordingly, the particles on the semiconductor wafer 13 can be effectively collected.

Further, in the particle collecting system 10 of the present embodiment, the wind speed of the gas between the particle collecting apparatus 20 and the semiconductor wafer is preferably 0.02 mm/sec or above, as described with reference to FIGS. 16 and 19, for example. Accordingly, the particles on the semiconductor wafer 13 can be effectively collected.

Further, in the particle collecting system 10 of the present embodiment, the ratio $Q_1/Q_2$ of the flow rate $Q_1$ of the gas supplied from the supply port 25 to the flow rate $Q_2$ of the gas sucked from the intake port 27 preferably satisfies the condition $1.0 \leq (Q_1/Q_2) \leq 1.2$ as described with reference to FIG. 13, for example. Accordingly, the particles on the semiconductor wafer 13 can be effectively collected.

Further, in the particle collecting system 10 of the present embodiment, the supply port 25 is inclined toward the central axis of the supply port 25 at the bottom of the housing 23. On the assumption that the radius of the bottom of the housing 23 is r and the distance between the bottom of the housing 23 and the semiconductor wafer 13 is $d_1$, the angle $\theta_2$ of the inclination of the supply port 25 with respect to the bottom surface of the housing 23 is preferably within a range specified by the above relation (2), as described with reference to FIG. 17, for example. Accordingly, the particles on the semiconductor wafer 13 can be effectively collected.

Further, in the particle collecting system 10 of the present embodiment, the gas supplied from the supply port 25 to the semiconductor wafer 13 is preferably dry air or inert gas. Accordingly, deformation of the surface of the semiconductor wafer 13 which is caused by the gas supplied from the supply port 25 onto the semiconductor wafer 13 can be suppressed.

(Other Applications)

The present disclosure is not limited to the above embodiment and may be variously modified within the scope thereof.

Figure 20:
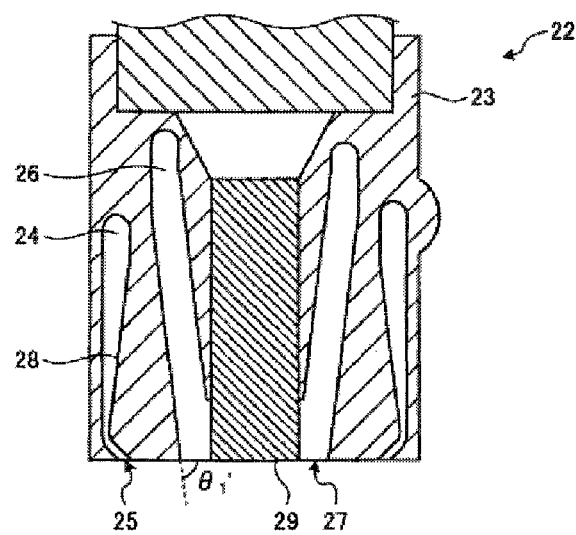
FIGS. 20 and 21 show other examples of the particle collecting apparatus.

For example, in the head 22 of the above embodiment, the angle $\theta_1$ between the inner surface of the partition plate 28 and the bottom surface of the housing 23 is greater than 90°, as can be seen from FIG. 3, for example. However, the disclosed technique is not limited thereto. In another example of the head 22, the angle $\theta_1$ between the inner surface of the partition plate 28 and the bottom surface of the housing 23 may be smaller than 90°, as can be seen from FIG. 20, for example. In that case, the collecting rate of 80% or above can be obtained as in the above embodiment.

In the head 22 of the above embodiment, the ceiling of the supply line 24 is gradually decreased while rotating about the central axis of the supply port 25 in a direction in which the gas supplied through the line 48 flows, as described with reference to FIGS. 3 to 8. Therefore, the gas flows in the supply line 24 in a spiral shape from top to bottom. The ceiling of the intake line 26 is gradually increased while rotating about the ultrasonic wave generator 29 in a direction in which the gas sucked from the intake port 27 flows. Accordingly, the gas flows in the intake line 26 in a spiral shape from bottom to top. However, the disclosed technique is not limited thereto.

Figure 21:
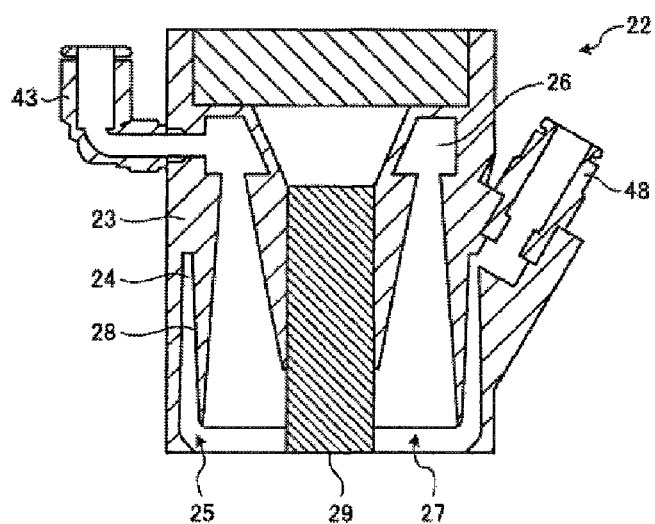

In another example, the supply line 24 and the intake line 26 have a substantially constant height as shown in FIG. 21, for example. In that case, the gas supplied into the supply line 24 through the line 48 flows from top to bottom while being diffused into the supply line 24 and then is supplied onto the semiconductor wafer 13 from the supply port 25 without rotating about the central axis of the supply port 25. The gas sucked from the intake port 27 flows from bottom to top in the intake line 26 without rotating about the ultrasonic wave generator 29 and then is sucked by the suction pump 40 through the line 43. In the head 22 configured as described above, the collecting rate of 80% or above can be obtained by setting the flow rate of the gas supplied from the supply port 25 and the flow rat of the gas sucked from the intake port 27 to be greater (by, e.g., three times or more) than the flow rates of the gases in the case of using the head 22 of the above embodiment.

Figure 22:
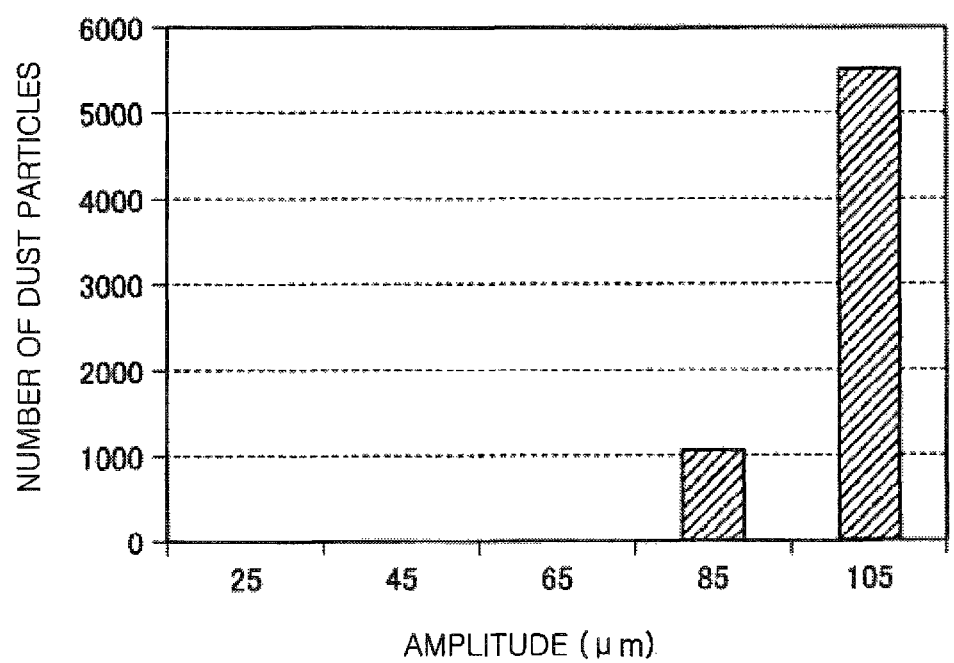
FIG. 22 shows exemplary relation between an amplitude of an ultrasonic wave and the number of dust particles.

In the above embodiment, the relation between the amplitude of the ultrasonic wave and the distance $d_2$ to the target object was measured in the following manner. First, the relation between the amplitude of the ultrasonic wave and the number of dust particles in the case of setting the distance $d_2$ between the ultrasonic wave generator 29 and the semiconductor wafer 13 to 5 mm was measured. FIG. 22 shows exemplary relation between the amplitude of the ultrasonic wave and the number of dust particles. Referring to FIG. 22, the number of dust particles is increased at an accelerated rate when the amplitude of the ultrasonic wave generated by the ultrasonic wave generator 29 becomes 85 μm or above.

Figure 23:
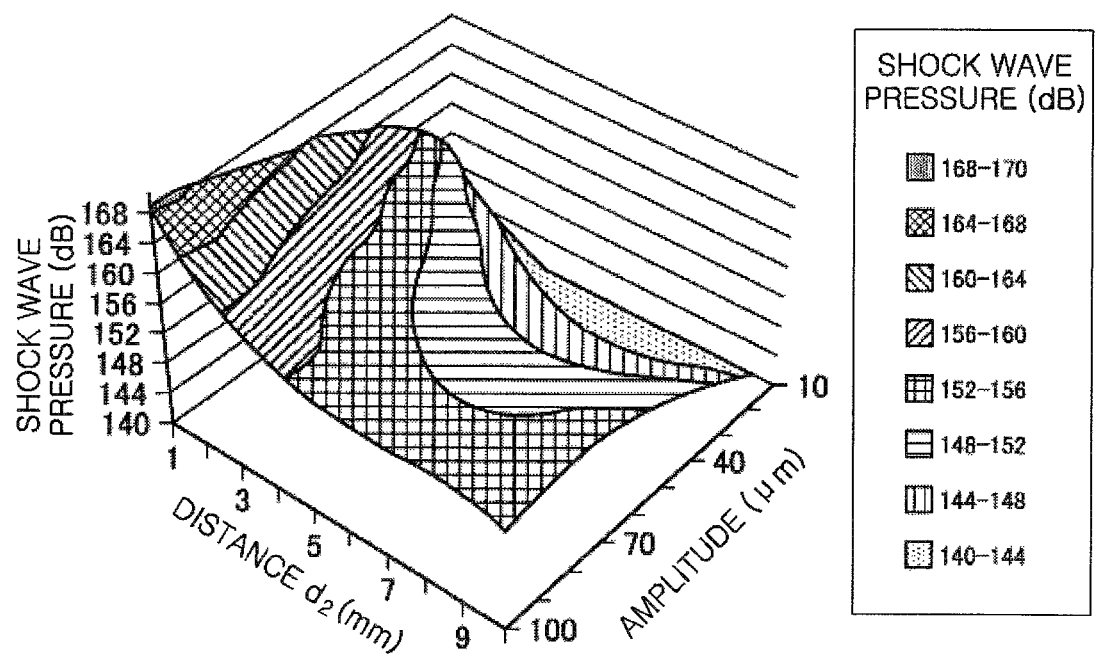
FIGS. 23 to 25 show exemplary relation among amplitude of an ultrasonic wave, a distance to the target object and a shock wave pressure.
Figure 24:
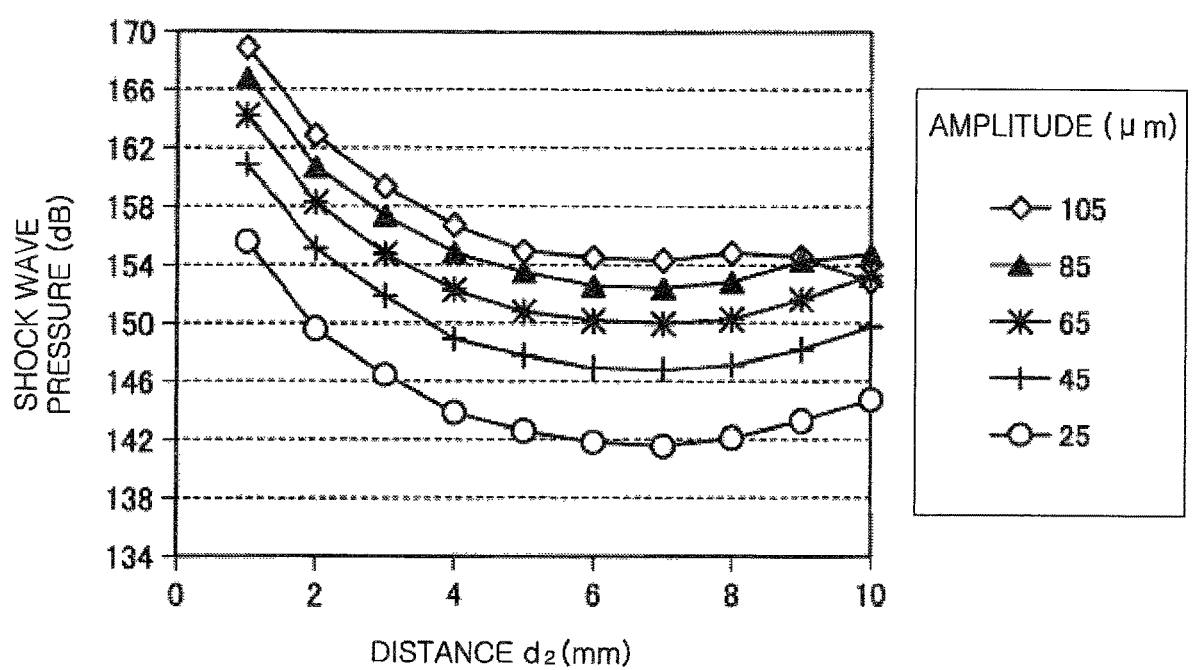
Figure 25:
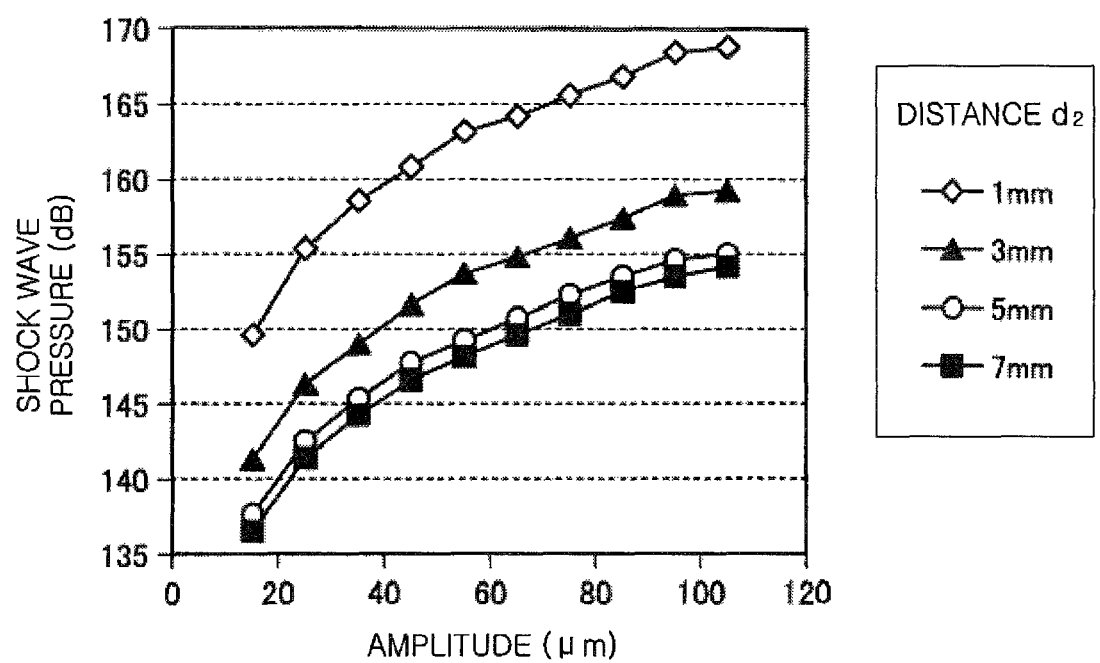

FIGS. 23 to 25 show exemplary relation between the amplitude of the ultrasonic wave, the distance $d_2$ to the target object and a shockwave pressure. As shown in FIGS. 23 to 25, for example, the shock wave pressure depends on two parameters, i.e., the distance $d_2$ from the ultrasonic wave generator 29 to the semiconductor wafer 13 as the target object 13 and the amplitude of the ultrasonic wave. The shock wave pressure is increased as the distance $d_2$ from the ultrasonic wave generator 29 to the semiconductor wafer is decreased. Further, the shock wave pressure is increased as the amplitude of the ultrasonic wave is increased.

Referring to FIGS. 24 and 25, for example, when the distance $d_2$ between the ultrasonic wave generator 29 and the semiconductor wafer 13 is 5 mm and the ultrasonic wave generator 29 generates an ultrasonic wave having an amplitude of 85 μm, the shock wave pressure becomes 153.6 dB. The shock wave pressure depends on the two parameters, i.e., the distance $d_2$ from the ultrasonic wave generator 29 to the semiconductor wafer 13 and the amplitude of the ultrasonic wave. When the shock wave pressure becomes 153.6 dB or above, the number of dust particles from the semiconductor wafer 13 is increased at an accelerated rate. According to further study of the present inventors, the number of dust particles from the semiconductor wafer 13 is increased at an accelerated rate when the shock wave pressure becomes 150 dB or above. The level of the shock wave pressure at which the dust particles are generated at an accelerated rate depends on a material or a manufacturing method of the target object. By controlling the number of dust particles in consideration of the shock wave pressure, it is possible to quantify optimal values of the distance $d_2$ between the ultrasonic wave generator 29 and the target object and the amplitude of the ultrasonic wave.

In the head 22 of the above-described embodiment, the ceiling of the supply line 24 is gradually decreased while rotating about the central axis of the supply port 25 in the gas flow direction and the ceiling of the intake line 26 is gradually increased while rotating about the ultrasonic wave generator 29 in the gas flow direction, as described with reference to FIGS. 3 to 8. However, the disclosed technique is not limited thereto. For example, a rib or a groove may be formed at the supply line 24 in a spiral shape from top to bottom along the outer wall surface of the partition plate 28 or the inner wall surface of the housing 23. Accordingly, the vortex flow can be more effectively generated in the supply line 24. Further, a rib or a groove may be formed at the intake line 26 in a spiral shape from bottom to top along the inner wall surface of the partition plate 28. Accordingly, the vortex flow can be more effectively generated in the intake line 26. As a result, the vortex flow of the gas can be more effectively generated between the particle collecting apparatus 20 and the semiconductor wafer 13.

In the head 22 of the above embodiment, the cylindrical ultrasonic wave generator 29 is generated at the substantially center thereof and the ultrasonic wave is emitted from the ultrasonic wave generator 29 to the semiconductor wafer 13 positioned therebelow. However, in another example, the ultrasonic wave generator 29 may generate no ultrasonic wave or a cylindrical member that does not generate an ultrasonic wave may be provided at the position of the ultrasonic wave generator 29. In that case as well, the particles on the semiconductor wafer 13 below the head 22 are effectively collected by the vortex flow of the gas supplied from the supply port 25 and the vortex flow of the gas sucked from the intake port 27.

While the disclosure has been shown and described with respect to the embodiments, it will be understood by those skilled in the art that various changes and modifications may be made without departing from the scope of the disclosure as defined in the following claims.

What is claimed is:

1. A particle collecting apparatus comprising:
 a cylindrical housing having a closed top and an open bottom facing a target object;
 a gap forming unit configured to form a gap having a predetermined distance between the bottom and the target object;
 a supply port formed at the opening of the bottom in an annular shape along an inner wall of the housing and configured to supply a gas to the target object;
 an intake port provided closer to a central axis of the supply port than the supply port and configured to suck particles on the target object;
 a cylindrical member disposed along a central axis of the supply port;
 a partition plate configured to partition a gas supplied to the supply port and a gas sucked from the intake port;
 a first flow path, through which a gas supplied from an outside of the housing flows toward the supply port, formed between an inner wall surface of the housing and an outer wall surface of the partition plate, the first flow path having a ceiling that is gradually decreased while rotating about the central axis of the supply port in a direction in which the gas supplied from the outside of the housing flows; and
 a second flow path, through which the gas sucked from the intake port flows toward the outside of the housing, formed between an inner wall surface of the partition plate and an outer wall surface of the cylindrical member, the second flow path having a ceiling that is gradually increased while rotating about the cylindrical member in a direction in which the gas sucked from the intake port flows.

2. The particle collecting apparatus of claim 1, wherein the cylindrical member is an ultrasonic wave generator configured to generate an ultrasonic wave toward the target object.

3. The particle collecting apparatus of claim 2, wherein a shock wave pressure applied to a surface of the target object by the ultrasonic wave generated by the ultrasonic wave generator is greater than or equal to 150 dB.

4. The particle collecting apparatus of claim 1, wherein the gas flowing through the first flow path flows from top to bottom while rotating in a predetermined direction along the inner wall surface of the housing about the central axis of the supply port, and
 the gas flowing through the second flow path flows from bottom to top while rotating in a direction same as the direction of the gas flows through the first flow path along the inner wall surface of the partition plate about the central axis of the intake port.

5. The particle collecting apparatus of claim 1, wherein a wind speed of a gas on the target object is greater than or equal to 0.02 mm/sec.

6. The particle collecting apparatus of claim 1, wherein a ratio of a flow rate of the gas supplied through the supply port to a flow rate of the gas sucked through the intake port is greater than or equal to 1.0 and smaller than or equal to 1.2.

7. The particle collecting apparatus of claim 1, wherein the housing has a substantially cylindrical shape,
 the supply port is inclined toward the central axis of the supply port at the bottom of the housing, and an angle of the inclination of the supply port with respect to the bottom of the housing is within a range specified by tan−1(d1/2r)<θ≤60°, wherein r is a radius of the bottom of the housing and d1 is a distance between the bottom of the housing and the target object.

8. The particle collecting apparatus of claim 1, wherein the gas supplied from the supply port is dry air or inert gas.

9. A particle collecting method by a particle collecting apparatus comprising:
forming a gap having a predetermined distance between a target object and a cylindrical housing having a closed top and an open bottom facing the target object;
supplying a gas to the target objet from a supply port formed at the opening of the bottom in an annular shape along an inner wall surface of the housing; and
sucking particles on the target object from an intake port positioned closer to a central axis of the supply port than the supply port;
wherein the particle collecting apparatus comprises:
a cylindrical member disposed along a central axis of the supply port;
a partition plate configured to partition a gas supplied to the supply port and a gas sucked from the intake port;
a first flow path, through which a gas supplied from an outside of the housing flows toward the supply port, formed between an inner wall surface of the housing and an outer wall surface of the partition plate, the first flow path having a ceiling that is gradually decreased while rotating about the central axis of the supply port in a direction in which the gas supplied from the outside of the housing flows; and
a second flow path, through which the gas sucked from the intake port flows toward the outside of the housing, formed between an inner wall surface of the partition plate and an outer wall surface of the cylindrical member, the second flow path having a ceiling that is gradually increased while rotating about the cylindrical member in a direction in which the gas sucked from the intake port flows.

10. A particle collecting system comprising:
a particle collecting apparatus;
a gas supply unit configured to supply a gas to the particle collecting apparatus;
a flow rate controller configured to control a flow rate of the gas supplied from the gas supply unit to the particle collecting apparatus;
a suction pump configured to suck the gas from the particle collecting apparatus; and
a flow speed meter configured to measure a flow speed of the gas sucked from the particle collecting apparatus by the suction pump,
wherein the particle collecting apparatus includes:
a cylindrical housing having a closed top and an open bottom facing a target object;
a gap forming unit configured to form a gap having a predetermined distance between the bottom and the target object;
a supply port formed at the opening of the bottom in an annular shape along an inner wall surface of the housing and configured to supply the gas supplied from the gas supply unit to the target object;
an intake port provided closer to a central axis of the supply port than the supply port and configured to suck a gas containing particles on the target object by suction of the suction pump;
cylindrical member disposed along a central axis of the supply port;
a partition plate configured to partition a gas supplied to the supply port and a gas sucked from the intake port;
a first flow path, through which a gas supplied from an outside of the housing flows toward the supply port, formed between an inner wall surface of the housing and an outer wall surface of the partition plate, the first flow path having a ceiling that is gradually decreased while rotating about the central axis of the supply port in a direction in which the gas supplied from the outside of the housing flows; and
a second flow path, through which the gas sucked from the intake port flows toward the outside of the housing, formed between an inner wall surface of the partition plate and an outer wall surface of the cylindrical member, the second flow path having a ceiling that is gradually increased while rotating about the cylindrical member in a direction in which the gas sucked from the intake port flows.

11. The particle collecting system of claim 10, further comprising:
a particle counter provided between the particle collecting apparatus and the flow speed meter and configured to measure the number of particles contained in a gas sucked through the particle collecting apparatus.

* * * * *